United States Patent
Fernández Martínez et al.

(10) Patent No.: US 8,506,079 B2
(45) Date of Patent: Aug. 13, 2013

(54) METHOD FOR THE BINOCULAR MEASUREMENT AND CONTROL OF EYE ABERRATIONS, SIMULTANEOUSLY PROVIDING VISUAL STIMULANTS, AND OPHTHALMIC INSTRUMENT IMPLEMENTING SAID METHOD

(75) Inventors: Enrique J. Fernández Martínez, Murcia (ES); Pedro Prieto Corrales, Murcia (ES); Pablo Artal Soriano, Murcia (ES)

(73) Assignee: Voptica S.L., Murcia (ES)

( * ) Notice: Subject to any disclaimer, the term of this patent is extended or adjusted under 35 U.S.C. 154(b) by 76 days.

(21) Appl. No.: 13/254,268

(22) PCT Filed: Mar. 4, 2010

(86) PCT No.: PCT/ES2010/000089
§ 371 (c)(1),
(2), (4) Date: Oct. 20, 2011

(87) PCT Pub. No.: WO2010/100298
PCT Pub. Date: Sep. 10, 2010

(65) Prior Publication Data
US 2012/0038884 A1    Feb. 16, 2012

(30) Foreign Application Priority Data
Mar. 4, 2009  (ES) .................................. 200900605

(51) Int. Cl.
*A61B 3/08* (2006.01)
*A61B 3/14* (2006.01)

(52) U.S. Cl.
USPC ............................ 351/201; 351/209; 351/210

(58) Field of Classification Search
USPC ................................................. 351/200–246
See application file for complete search history.

(56) References Cited

U.S. PATENT DOCUMENTS

| | | | |
|---|---|---|---|
| 6,598,974 B2 * | 7/2003 | Jones et al. | 351/221 |
| 2004/0100619 A1 | 5/2004 | Olivier et al. | |
| 2007/0139614 A1 * | 6/2007 | Lindacher | 351/212 |
| 2008/0246921 A1 | 10/2008 | Mihashi et al. | |
| 2011/0279778 A1 * | 11/2011 | Saito | 351/221 |

FOREIGN PATENT DOCUMENTS

| WO | 01/82791 A1 | 11/2001 |
|---|---|---|
| WO | 03/022140 A2 | 3/2003 |

* cited by examiner

*Primary Examiner* — Mohammed Hasan
(74) *Attorney, Agent, or Firm* — Ladas & Parry LLP

(57) ABSTRACT

The invention relates to an ophthalmic instrument and method for measuring, controlling, and handling aberrations (1) of the eyes (2, 3), which further simultaneously provide visual stimulants when operating same. The instrument consists of a single device for correcting aberrations (4) as well as a single aberration sensor (5), optically connected by an optical system (14). A lighting system (9) introduces beams of light into both eyes. The measurement, control, and handling of the aberrations (1), as well as the providing of visual stimulants (6), are simultaneously and binocularly (7, 8) carried out.

29 Claims, 6 Drawing Sheets

METHOD FOR THE BINOCULAR MEASUREMENT AND CONTROL OF EYE ABERRATIONS, SIMULTANEOUSLY PROVIDING VISUAL STIMULANTS, AND OPHTHALMIC INSTRUMENT IMPLEMENTING SAID METHOD

FIELD OF THE INVENTION

The present invention refers to an instrument and method for binocular measurement and control of aberrations present in the human eye, which also allows the presentation of visual stimuli in a manner simultaneous to the operation of the rest of the method. Thus the invention refers to a method that incorporates so called adaptive optics as a technology capable of effectively acting on the wavefront of each eye in a controlled manner so as to manipulate aberrations in the eyes.

The invention is related to the objective measurement of the optical quality of the eyes in a binocular manner. Thus it is found in the field of instruments having a biomedical character that are employed for the study, diagnosis or characterization of a given process, sense or organ of the human being. The described method is likewise related to the measurement of subjective visual quality by means of tests or of carrying out of visual tasks which are affected by the optical quality of the eyes, that is, by their aberrations. In any event these are measurements that are also made in an objective manner. Said eye aberrations can be eliminated, either totally or partially, and also induced to a greater or less degree in a controlled manner. Consequently the invention refers to an instrument that enables the integral study, characterization and diagnosis of vision quality, both from an objective and purely optical standpoint by the measurement of the aberrations, as well as from a subjective or perceptive point of view by means of visual tests conducted in controlled conditions, using each eye separately or both eyes in a binocular manner.

The invention explicitly describes the practical embodiment of an ophthalmic instrument and its equivalent variants that produce the same effect which implement said method.

BACKGROUND OF THE INVENTION

Vision is a complex phenomenon that involves different stages, all closely interrelated. In a first stage the images of the objects that comprise the scene that surrounds the subject is formed on his retina, an organ located at the back of the eye. Afterwards, in a different stage, the retina converts the images into electric impulses and physical-chemical signals that are sent to the brain by means of specialized neurons. The last level of the process occurs in the brain, which is where the interpretation of the image is produced through diverse psychological processes that lead to the final perception of the objects that initially provoked the visual phenomenon. In the first stage, commonly referred to as the optical stage, the quality of the images produced on the retina is received through the aberrations that the optics of the eye introduce, this being understood as an image forming system. Thus the interest in measuring and correcting aberrations in the eye is basic in the context of vision. In human beings vision is binocular, carried out through the cooperation of both eyes. This implies a series of improvements and advantageous characteristics in relation to the end perception of the object with respect to the monocular case, in which vision is carried out through a single eye.

The objective measurement of aberrations of the wavefront and their correction by means of adaptive optics, understood as compensation in real time, has been described in the case of the human eye from the beginnings of the XXI century. Thus the work of E. J. Fernández, I. Iglesias, and P. Artal, "Closed-loop adaptive optics in the human eye", Opt. Lett., 26, 746-748 (2001) contains a first practical implementation of an experimental measurement system using a Hartman-Shack type wavefront system and an electrostatic deformable membrane mirror to obtain compensations of aberrations of the eye in real time. Out of all of the existing means for wavefront measurement, nowadays the Hartmann-Shack sensor is the most used in the context of the optics of the eye. It was originally introduced in the works of J. Liang, B. Grimm, S. Goelz, and J. F. Bille, "Objective measurement of WA's of the human eye with the use of a Hartmann-Shack wave-front sensor," J. Opt. Soc. Am. A 11, 1949-1957 (1994); J. Liang and D. R. Williams, "Aberrations and retinal image quality of the normal human eye," J. Opt. Soc. Am. A 14, 2873-2883 (1997); as well as P. M. Prieto, F. Vargas-Martin, S. Goelz, P. Artal, "Analysis of the performance of the Hartmann-Shack sensor in the human eye", J. Opt. Soc. Am. A, 17, 1388-1398 (2000). Since then it has been employed intensively in the field of ophthalmic optics.

One application of adaptive optics of great practical interest is its use in visual simulators. The concept was originally described in the article of E. J. Fernández, S. Manzanera, P. Piers, P. Artal, "Adaptive optics visual simulator", J. Refrac. Surgery, 18, S634-S638 (2002). The application is based on emulating some established optical conditions in a controlled manner and recording the perception of the subject to some stimuli or given visual tasks. In this way valuable information is obtained regarding the relation between optical quality, in terms of the aberrations, and visual quality.

New effects related to the above concept have been obtained recently, such as those shown in the article P. Artal, L. Chen, E. J. Fernández, B. Singer, S. Manzanera, D. R. Williams, "Neural compensation for the eye's optical aberrations", J. Vis., 4, 281-287 (2004). The concept of visual stimulation by means of adaptive optics has also been successfully demonstrated for purposes of designing ophthalmic elements.

Specific examples applied to intraocular lenses and contact lenses are found in P. A. Piers, E. J. Fernández, S. Manzanera, S. Norrby, P. Artal, "Adaptive optics simulation of intraocular lenses with modified spherical aberration", Invest. Ophthalmol. Vis. Sci., 45, 4601-4610 (2004) and S. Manzanera, P. M. Prieto, D. B. Ayala, J. M. Lindacher, P. Artal, "Liquid crystal Adaptive Optics Visual Simulator: Application to testing and design of ophthalmic optical elements", Opt. Express, 15, 16177-16188 (2007).

Different patents have likewise disclosed the use of adaptive optics in the study and characterization of vision and, more specifically, in the analysis of optical aberrations of the eye. The measurement of aberrations has been used for their subsequent correction by means of deformable mirrors or phase modulators, analysis of the refraction in the eye and its subsequent compensation with ophthalmic, contact, or intraocular lenses, and low level methods of correction in general. Thus Document U.S. Pat. No. 6,155,684 discloses a method for subjective measurement of aberrations of the eye and their subsequent or simultaneous compensation. The invention makes possible to estimate the refractive error in the eye and, consequently, the required prescription for correcting it. This method can only be used under monocular vision.

Another example is found in Document U.S. Pat. No. 6,379,005 B1, which discloses an adaptive optical system specifically for use in the human eye. This includes a measurement of aberrations of the eye by means of a Hartmann-Shack sensor and its subsequent correction by means of a deformable mirror. The procedure is proposed for the prescription of ophthalmic and intraocular lenses, and even for refractive surgery. The instrument can only be applied to a single eye. Its extension to the binocular case requires a duplication of each and every one of its components.

Along the same lines Document U.S. Pat. No. 6,722,767 B2 discloses a method that combines adaptive optics by means of a corrector element that introduces aberrations in a controlled manner, with the subjective response of the subject to the degradation of visual stimulation presented—all of this under monocular conditions. Its employment in binocular vision requires replicating the experimental system that implements the described method.

Document U.S. Pat. No. 6,709,108 describes a method for objective measurement of aberrations of the eye and its subsequent optical compensation by means of an initial correction of the focus and another additional correction of the rest of the aberrations. The method enables prescribing ordinary low level ophthalmic prescriptions such as eyeglasses and contact lenses under monocular conditions.

Document U.S. Pat. No. 6,964,480 B2 discloses a design that allows compensating aberrations of the eye in two clearly distinct steps after the aberrations have been measured by the instrument itself, or estimated by any other method. In a first step the defocus is compensated, leaving the rest of the high order aberrations to be corrected by a deformable mirror. The assembly can only be applied to one eye at a time.

Exploiting a similar concept, Document U.S. Pat. No. 7,128,416 B2 discloses a method and instrument for implementing it, capable of estimating the refraction based on objective measurements of aberrations of the eye and modifying said aberrations by means of adaptive optics. This is carried out under strictly monocular conditions.

Later in time Document U.S. Pat. No. 7,195,354 B2 was published, in which a method is proposed, together with its corresponding practical embodiment in the form of an electro-optic system that allows measuring the aberrations of the eye so as to compensate them by means of a correction device, which enables the subject to have simultaneous vision of visual stimuli. In this way a method is provided for enabling the subject to see through a corrected optic. The manner in which said invention is disclosed makes clear that the method only works under monocular vision. Thus its possible application under binocular vision requires duplicating the entire experimental system.

Other alternative methods for the correction of the wavefront by means of adaptive optics in the context of visual and ophthalmic optics have recently been proposed, as it can be seen in U.S. Pat. No. 7,350,920 B2, which applies new designs for implementing objective measurements of aberrations of the eye and their correction. The invention per se is only applicable under monocular vision.

In the current state of the art, as shown in the patents described above, one constant is the use of adaptive optics under exclusively monocular conditions. However, the vision of human beings is obviously binocular, and the interaction of both eyes in the final perception of the images is basic. Consequently, in the context of vision the above methods only provide a partial solution to the problem of assessing optical quality and its correction. Thus the result is that for the possible application of all of the methods known to date in binocular conditions, it is necessary to duplicate the experimental systems. This entails increasing the complexity of the electro-optical systems and increasing costs, which in practice makes simultaneous use in both eyes unreasonable. The invention disclosed in this document resolves this basic problem, enabling the measurement and compensation, and in general the manipulation, of aberrations of the eyes in a binocular manner employing a single aberration correction device and a single sensor of aberrations. Furthermore, the method provides a way of showing visual stimuli in a manner simultaneous with the operation of the rest of the system.

SUMMARY OF THE INVENTION

The present invention discloses a method for measurement of aberrations in the eyes of a subject by means of a single wavefront sensor in a binocular and simultaneous manner and their control with a single aberration correction device. The manipulation of the aberrations of the subject can be employed to attain the complete correction of those, partial correction of only certain aberrations or, in general, in the partial addition or compensation of any optical aberration, without limits. The induction of wavefronts of any nature is also possible. The method also enables simultaneous presentation of visual stimuli, whose perception is affected by the combination of aberrations pertaining to the subject and those introduced or compensated by the aberration correction device, all of this in a controlled manner by means of the sensor. In this way the method disclosed in the invention enables the testing and total or partial evaluation of the visual capacity of a subject in a binocular manner in the presence or absence of aberrations, said aberrations being controlled by the aberration correction device and the wavefront sensor. Furthermore, the method enables the natural objective measurement of aberrations in a binocular manner, and, as such, the objective assessment of the visual quality of the subject being measured.

The invention also refers to a variety of ophthalmic instruments for the measurement and manipulation of aberrations of the eyes in a binocular manner, both in its open loop and closed loop versions, and the simultaneous presentation of the visual stimuli that employ the previous method.

Other features and advantages of the present invention will be disclosed in the following detailed description that outlines an illustrative embodiment of its object in relation to the accompanying figures.

In particular, the invention describes an ophthalmic instrument for the measurement, control and manipulation of aberrations of the eyes that enables simultaneous presentation of visual stimuli. It comprises a retinal illumination system, a single aberration correction device, as well as a single aberration sensor (the last two elements optically conjugated to each other by means of an optical system), in which the operations of measurement, control and manipulation of aberrations and presentation of stimuli are carried out in a simultaneous and binocular manner.

In one configuration of the instrument, the control of the aberration correction device is carried out in a closed loop based on wavefront measurements obtained by the sensor, which include the aberrations of the subject and those introduced by the aberration correction device.

In an alternative configuration of the instrument the control of the aberration correction device is carried out in an open loop based on wavefront measurements obtained by the sensor, which only include the aberrations of the subject.

The visual stimuli are projected on the retinas of the subject in a binocular and simultaneous manner with the operation of the measurement and manipulation of the aberrations of the eyes of the subject, and are affected by the aberrations introduced by the aberration correction device.

The control and manipulation of defocus can be carried out by means of a Badal optometer or by the aberration correction device.

The control and monitoring of the two pupils is conducted simultaneously by means of a single camera.

The aberration correction device can be a deformable bimorph mirror, an electrostatic deformable mirror, a segmented deformable mirror, a deformable mirror based on independently actuated micro-mirrors, a liquid crystal phase modulator, a ferroelectric liquid crystal phase modulator, or a liquid crystal phase modulator on silicon.

At the same time, the wavefront sensor can be a Hartmann-Shack type, a pyramid type wavefront sensor, a wavefront sensor type based on curvature measurement, a sensor that employs interferometry, a sensor of the type that employs double-passed retinal images, a Tscheming type sensor or a crossed cylinder type sensor.

The light source employed in the ophthalmic instrument for measurement, control and manipulation of the aberrations of the eyes can be a laser source that emits in the visible light spectrum, a laser source that emits in the infrared spectrum outside of the visible range, a thermal source in the visible spectrum, or a thermal source that emits in the infrared spectrum outside the visible range.

The control of the trajectory of the two light beams on the eyes can be carried out by:

reflections in a mirrored prism and two independent mirrors whose placement and relative angles can be manipulated.

refractions in prisms whose placement and relative angles can be manipulated a combination of prisms and mirrors whose placement and relative angles can be manipulated.

The invention also discloses a method of measurement, control, and manipulation of aberrations of the eyes that employs the ophthalmic instrument disclosed in the present document.

Figure 1:
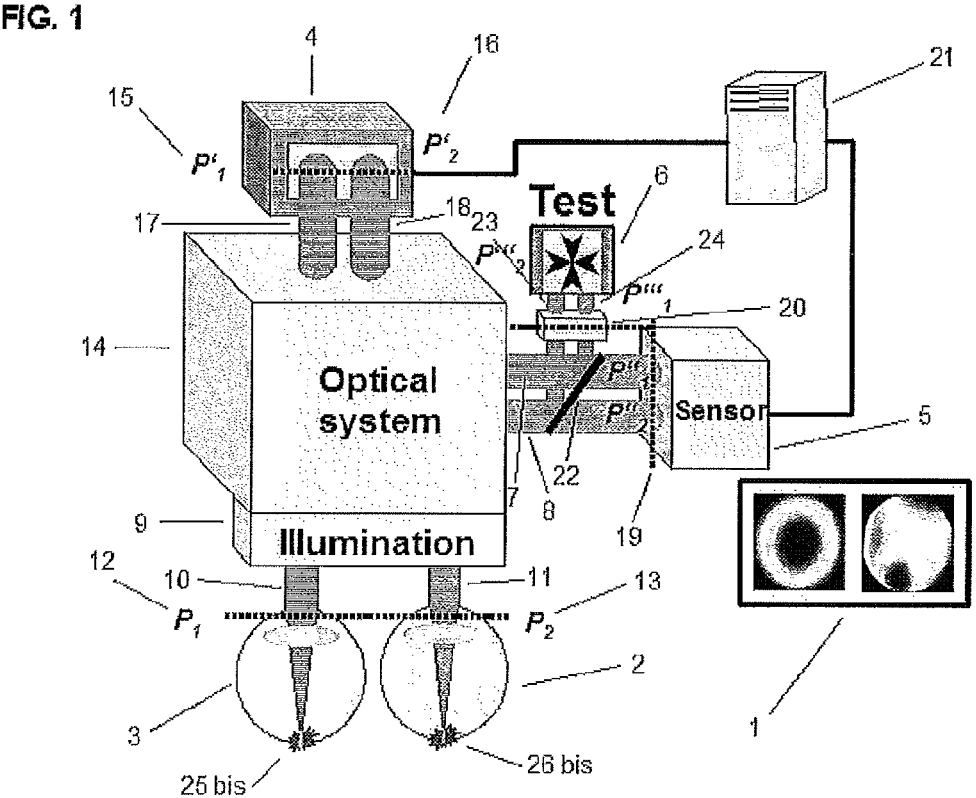
FIG. 1 displays a schematic diagram of the basic parts required for putting into practice the method of measurement and control of ocular aberrations in a binocular manner in accordance with the present invention. The diagram also incorporates the additional path for presenting stimuli or carrying out visual tasks.

The following numbered references are linked to the different physical elements forming part of the invention, which will be seen throughout the present document:

1. Aberrations
2. Eye
3. Eye
4. Aberration correction device
5. Aberration (or wavefront) sensor
6. Stimuli.
7. Beam emerging from eye 3, together with 8
8. Beam emerging from eye 2, together with 7
9. Simultaneous illumination system of eyes 2, 3
10. Fraction of light sent out from eye 3, together with 11
11. Fraction of light sent out from eye 2, together with 10
12. Plane of the output pupil of eye 3
13. Plane of the output pupil of eye 2
14. Optical system
15. Image of 12 on the plane of aberration correction device 4
16. Image of 13 on the plane of aberration correction device 4
17. Beam of light emerging from eye 3, together with 18
18. Beam of light emerging from eye 2, together with 17
19. Plane of the aberration sensor.
20. Plane of the output pupil for stimuli presentation
21. Computer
22. Beam splitter
23. Beam of light emerging from eye 2, together with 24
24. Beam of light emerging from eye 3, together with 22
25. Eye
25 bis. Retina of the eye
26. Eye.
26 bis. Retina of the eye
27. Light source
28. Illumination mask
29. Light source collimator 27
30. Beam splitter
31. Reflective prism
32. Mirror
33. Mirror
34. Light beam for the eye 26, together with 34 bis.
34 bis. Light beam for the eye 25, together with 34
35. System lens
36. System lens
37. Aberration correction device
38. Image from the output pupil of eye 25
39. Image from the output pupil of eye 26
40. Mirror plane
41. Mirror plane
42. Mirror plane
43. Mobile system or mechanized assembly
44. System lens
45. System lens
46. Wavefront sensor or aberrometer
47. Beam splitter
48. Stimuli presentation mask
49. Screen for presenting stimuli
50. Control camera of the pupil
51. Beam splitter
52. Wave front sensor or aberrometer
53. Lens
54. Lens
55. Beam splitter
56. Aberration correction device 57. Lens
57 bis. Lens
58. Lens
59. Mask for presenting stimuli
60. Visual stimulus
61. Image from the Hartmann-Shack sensor of eye 25, together with 62
62. Image from the Hartmann-Shack sensor of eye 26, together with 61
63. Prism
64. Prism
65. Prism
66. Prism
67. Optical system that produces two separated beams

DETAILED DESCRIPTION OF A FORM OF THE PREFERRED EMBODIMENT OF THE INVENTION

The disclosed invention consists in the measurement and control of aberrations (1) of eyes (2, 3) in a binocular and simultaneous manner, such as is shown in FIG. 1. One of the most noteworthy advantages of the invention in its practical application is based on the utilization of a single aberration correction device (4), as well as a single aberration sensor (5). Furthermore, its implementation enables the incorporation of an additional via for stimuli presentation (6), likewise in a binocular manner (7, 8). The embodiment of the present invention incorporates a subsystem of simultaneous illumination (9) of eyes (2, 3). A fraction of the light introduced into eyes (2, 3) is diffused by retinas (25 bis, 26 bis) and sent back to the exterior (10, 11).

Exit pupils (12, 13) of eyes (2, 3) (understood as the real or virtual pupils which effectively limit the quantity of light that emerges from an optical system), which are located on planes $P_1$ and $P_2$, conjugate optically by means of optical system (14) dedicated to this purpose on the surface of aberration correction device (4), in such a way that both pupils (12, 13) have their optical image (15, 16) on planes $P'_1$ and $P'_2$ on said aberration correction device (4). Optical system (14) guarantees that light beams (17, 18) emerging from the eyes (2, 3) do not overlap on aberration correction device (4), but rather that they arrive separated or spatially resolved. In this way independent and simultaneous actuation of the wavefront in a binocular manner is carried out. Optical system (14) guarantees and, in a similar manner, thus enables the two light beams (17, 18) emerging from pupils (10, 11) to reach sensor or aberrometer (5). In any event, optical system (14) guarantees that output pupils (12,13) of eyes (3,2) located on planes $P_1$ and $P_2$ conjugate on the surface of detector (19), which comprises the sensor or aberrometer of the two differentiated beams on $P'''_1$ y $P'''_2$. The assembly embodied by the invention thus guarantees that the plane of aberration correction device (4) and sensor (5) are also conjugated optically. The control of the aberrations of the eyes in a binocular form can be carried out by means of computer (21) which processes the measurements of the wavefront of fraction of light (10, 11) sent to the exterior from eyes (2, 3) and, possibly, employs said information in the correction, or in general in the control of aberrations (1) when passing through aberration correction device (4). The incorporation of a path for the presentation of stimuli (6) in a binocular manner is implemented by means of the beam splitter (22) corresponding to eyes (2, 3). The light emitted from stimuli (6) travels inverse path (7, 8) towards eyes (2, 3). This is carried out through conjugated planes $P'''_1$ and $P'''_2$ (23, 24), which limit the quantity of light emitted from stimuli (6). Visual stimulation (6) can be presented by means of one or various screens if an independent path is required for each eye.

Figure 2:
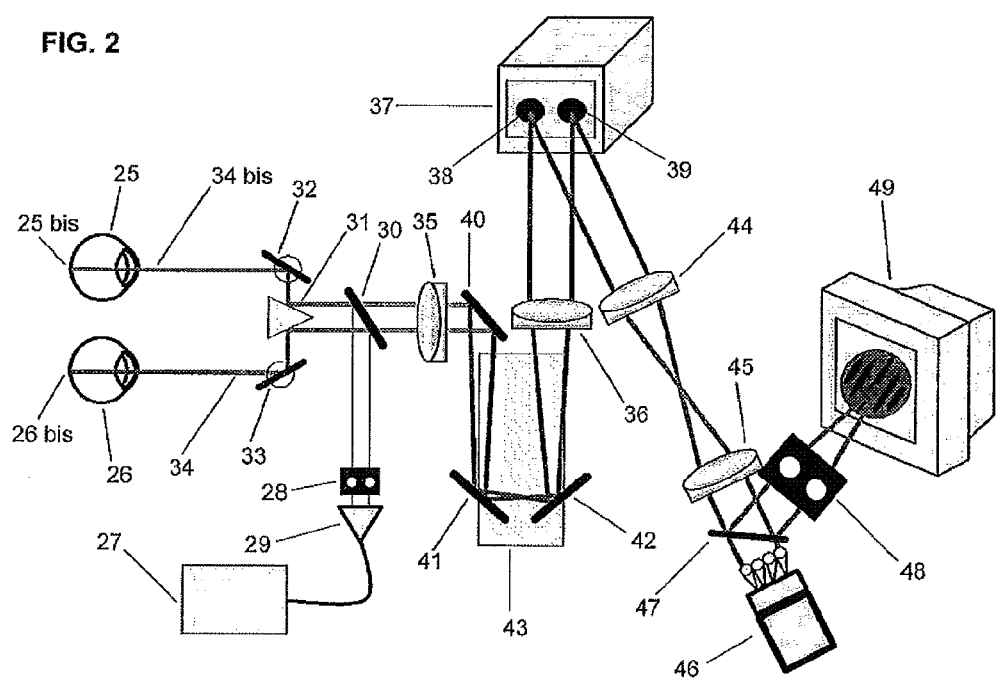
FIG. 2 displays a schematic draft of the main components for putting into practice the method of measurement and control of ocular aberrations and presentation of visual stimuli in accordance with the present invention in its operation in a closed loop mode.

As can be seen in FIG. 2, the illumination of eyes (25, 26) is carried out in a simultaneous manner with the object assembly of this invention by means of a light source (27), that can be a laser or a thermal source, preferably in infrared wavelengths or infrared wavelengths outside of the visible spectrum. In this way the subject does not perceive the measurement beam that strikes his retina in the event of parallel visual tasks being conduct. By means of mask (28), endowed with two orifices, collimated beam (29) emitted from light source (27) is distributed into two differentiated beams. These reach beam splitter (30) that can operate separating the spectral components exactly as is done by dichroic mirrors, polarization states, or distributing and uniformly transmitting the reflected incident light in a given fixed fraction. The light in the shape of two differentiated beams reflected by beam splitter (30) is redirected to eyes (25, 26) of the subject. In its path, the trajectory of the beams encounters a prism operating in total reflection (31), or possibly two mirrors that produce the same effect of separating the beams in a perpendicular direction, in general different, to the original incident one. Prism (31) is mounted on a mechanical holder that enables its displacement so as to control the separation of the reflected beams. At the same time, it can incorporate tilt movements of its planes, thus facilitating the fine tuning of the final direction of the two beams.

After the two beams are reflected in prism (31) said beams are again reflected by mirrors (32, 33). In this way the beams return to the initial direction of propagation before striking prism (31). Mirrors (32, 33) are mounted on a holder that enables their movement in the direction of the striking light, actuating on its actual separation. In this way it is possible to adjust the distance between beams (34, 34 bis) that are going to strike and penetrate eyes (25, 26) of the subject located in front of the system. The output pupils of the subject must be placed at the focal distance of the first system lens (35). Said lens can be interchanged with a spherical or parabolic mirror having the same effect. The fraction of light reflected or back-scattered in the two retinas of the subject makes the opposite path to that made by the two beams following their reflection in light splitter (30) mentioned above, a portion that constitutes the so called illumination subsystem (9), and separately penetrate optical system (14).

By means of lens (35, 36) following in the direction of the light, optically conjugation of the exit pupils of the subject is obtained on the surface of aberration correction device (37). This can be a deformable mirror of one of the existing types, or preferably a phase modulator based on liquid crystal. Thus clearly distinguishable images from the two pupils of the subject, corresponding to each eye, are formed on the aberration correction device. For this to occur the two preceding lenses must function as an optical telescope, and aberration correction device (37) must be placed at the focal distance of the lens that precedes it (36). This may be replaced by a spherical or parabolic mirror having the same effect. The effect of the telescopic system formed by lenses (35, 36) consists in forming the images of exit pupils (38, 39) of eyes (35, 26) on the aberration correction device (37).

Between lenses (35, 36), which form the telescope that precedes aberration correction device (37), a subsystem can be mounted that enables controlling the defocus in an independent manner. For this the configuration disclosed in FIG. 2 can be chosen, also known as the Badal system or Thorner optometer. In this configuration some flat mirrors (40, 41, 42) redirect the light in such a way that by actuating on the mount

(43) of the two mirrors normally aligned with each other (41, 42) the effective distance between the lenses that limit it (35, 36) can be varied, introducing in this way a defocus that depends on said separation. By means of two lenses (44, 45), in accordance with the direction of the light and from aberration correction device (37), as appears in FIG. 2, the surface of aberration correction device (37) is conjugated with the surface of wavefront sensor (46). In the place of lenses, spherical or parabolic mirrors having the same effect can be used.

Wavefront sensor (46) can be any of the existing types, preferably the Hartmann-Shack type. In it, the incident wavefront is estimated on the basis of the measurements of local slopes of the same, an operation that is carried out by sampling the wavefront with an array of microlenses. In the configuration that implements the invention, the wavefronts corresponding to each of the pupils form their images separately, although simultaneously, on the surface of sensor (46). A beam splitter (47), which may be operated by separating spectral components exactly as is done by dichroic mirrors, polarization states, or distributing and uniformly transmitting the reflected incident light in a given fixed fraction, directs the two incident beams towards the plane occupied by mask (48). Said mask (48) is placed preferably at the focal distance of the last lens (45) located before beam splitter (47) of the assembly in the described direction of the light. This way ensures that mask (48) occupies a plane conjugated to the plane of the output pupils of the subject. Mask (48) comprises a pair of orifices, the diameter and separation of which can be variable, and perhaps dependent on the relation of the total increase between the plane which contains them and the plane of the output pupils of the subject.

Behind mask (48) screen (49) is placed, or, possibly, screens, which show the visual stimuli that the subject can perceive in a binocular manner and simultaneously with the measurement and manipulation of the wavefronts of each of his eyes. The previously described configuration, and basically shown in FIG. 2, enables actuating on the wave front in closed loop. That is, the measurement of the aberrations of eyes (25, 26) already includes the effect aberration correction device (37) has introduced on them. Therefore it can be operated in an iterative manner and with high precision, until the desired aberrations are obtained or, possibly, their theoretical correction. This can be efficiently carried out by means of a sole processor that simultaneously controls the measurement of aberrations (1) and the phase introduced by aberration correction device (37).

An alternative practice for implementing the present invention consists in a system that operates under open loop configuration, in such a way that the measurement of aberrations (1) does not include the effect of aberration correction device (37). This is graphically depicted in FIG. 3. The illumination of the pupils and subsequent redirecting of the light emerging from retinas (25 bis, 26 bis) of eyes (25, 26) of the subject is carried out in an manner analogous to that previously described, in accordance to what has been detailed in FIG. 2. Camera (50) can operate in the monitoring of the position of the pupils of the subject, deriving part of the light reflected by them by means of beam splitter (51), of any of the previously described types (30, 47). This can be positioned in any plane of the experimental system which enables obtaining the image of the pupils, preferably in the illumination path, which obtains the reduction of possible losses of the light emerging from the retinas of the subject.

In the open loop mode the light that enters optical system (14) is conjugated on the surface of wavefront sensor (5, 52) by means of a telescope formed by two lenses (53, 54). These may be replaced by spherical or parabolic mirrors having the same effect. In this way, a Badal or Thorner optometer subsystem can be incorporated between them defined by elements (35, 36, 40, 41, 42, 43) as appear in FIG. 2, to control the blurring, as has been explained in the description of the implementation of the invention in the closed loop version. Between the two lenses (53, 54) beam splitter (55), of any of the types previously referred to (30, 47), may be placed. Beams (34, 34 bis) emerging from eyes (25, 26) are sent towards aberration correction device (56). Lens (57), or a spherical or parabolic mirror, enables conjugating the output pupils of the eyes of the subject on the surface of aberration correction device (56). Afterwards the beams can follow a similar path as described previously in the device operating in closed loop mode. A pair of lenses (57 bis, 58), or equivalent mirrors with focusing capacity, actuating as a telescope, conjugate the two pupils projected on aberration correction device (56) in mask (59), which limits the size of the beams that effectively reach visual stimulus (60). These are equivalent to those described for the purpose of the implementation in closed loop mode (48, 49), described in FIG. 2.

Figure 4:
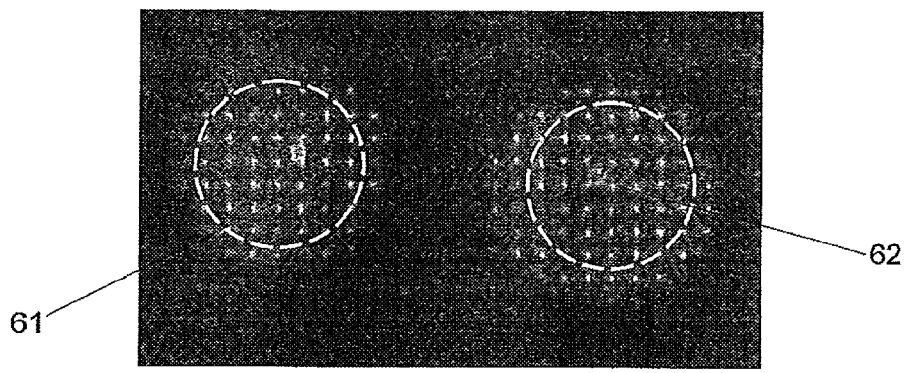
FIG. 4 displays, as a practical example of the method disclosed in the present invention, an image taken by the Hartmann-Shack sensor or aberrometer of the two pupils from a real subject. The analysis in binocular form of the aberrations is obtained by a single image and sensor. The image is recorded by means of an instrument that incorporates the features described in the present invention in its operating in an open loop mode.

The possibility of recording the aberrations of the two eyes in a single image is shown in FIG. 4. In the figure the typical point structures of a Hartmann-Shack sensor (61, 62) appear, which enable the obtention of the aberration of the wave for each one of the eyes of the subject. For the obtention of said image a device similar to that described in FIG. 1 was used, which, in principle, enables operation in closed loop. The practical interest of the described method is justified by the substantial reduction of the equipment needed for the measurement of the aberrations of the eye that may be carried out with a single camera. The efficiency of the algorithms for estimating the wave front on the basis of the displacement of the centroids in a Hartmann-Shack image is such that operation in real time is perfectly possible. This is of interest for studying the dynamics of the eye in binocular conditions.

Figure 3:
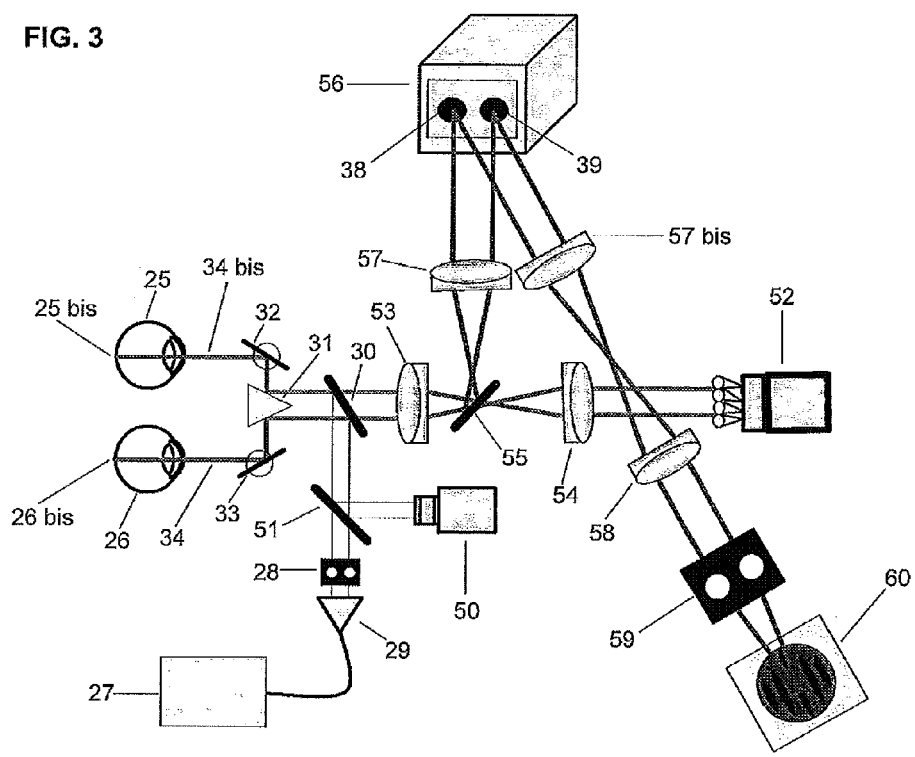
FIG. 3 displays a schematic diagram of the main components for putting into practice the method of measurement and control of ocular aberrations and presentation of visual stimuli in accordance with the present invention in its operation in an open loop mode.
Figure 5:
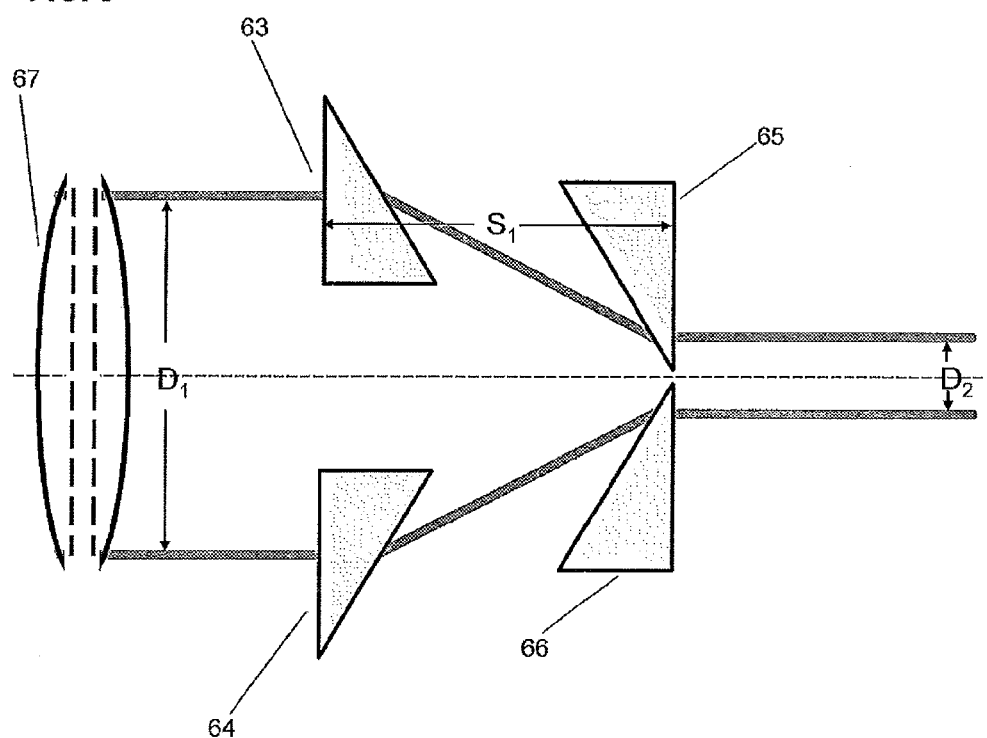
FIG. 5 displays a schematic diagram based only on refractive elements of an alternate subsystem to that described in previous FIGS. 2 and 3 for the simultaneous introduction of light from the eyes in the binocular measurement and control system of ocular aberrations.

One of the basic parts for the adequate implementation of the present invention is illumination subsystem (9). This should permit adjusting the distance of the beams that illuminate the two pupils to the interpupillary distance of each particular subject. It is likewise important to endow the subsystem with the degrees of freedom required so that the subject may have the possibility of being able to merge the images that his retinas receive emitted from stimulus (6) into a single binocular perception. In FIGS. 2 and 3 an implementation has been described and explicitly displayed that is based on the use of reflective prism (31) and two mirrors (32, 33). Another alternative that obtains an identical effect is employing prisms operating in transmission (63, 64, 65, 66), as displayed in FIG. 5. Preferably these are thin prisms, meaning that the deviation produced on the incident beam can be approximated depending on their refractive index. In accordance with FIG. 5, the light emerging from the two pupils, or, in general, from a system (67) that separates or produces two differentiated light beams, separated by a distance $D_1$, can be controlled by means of a system that enables adjusting the final separation between said beams $D_2$. For this, it suffices actuating on distance $S_1$ in accordance with FIG. 5. In this way, by adjusting in separation the position of the prism pair (63, 64) with respect to the other (65, 66), the desired effect is obtained. Preferably this subsystem can be incorporated within illumination subsystem (9), although it can also be incorporated with the same effect in any other situation of the optical system, as long as the beams emerging from the eyes are in parallel.

Figure 6:
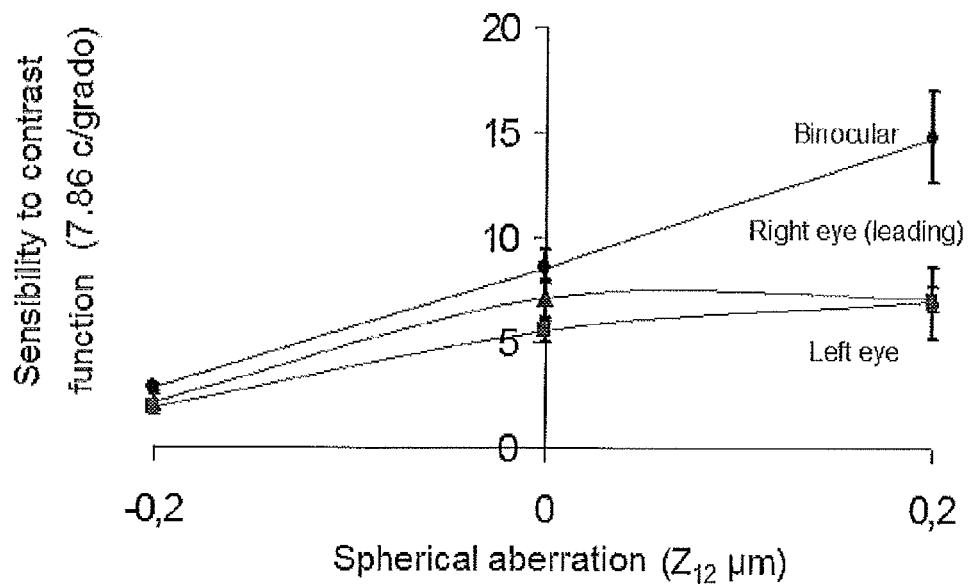
FIG. 6 displays the results of a real subject obtained by means of an experimental system such as the one described in FIG. 2, corresponding to operation in closed loop mode, in relation to the measurement of the sensibility to contrast function.

An example of the application and potential of the disclosed method in the context of the present invention is found in FIG. 6, which displays the results obtained in a real subject by means of an experimental system such as the one described in FIG. 2, corresponding to the closed loop operating mode in relative to the measurement of contrast sensitivity function. A frequency of 7.86 cycles per degree was selected for the measurement of closed loop contrast sensitivity. A consistent stimulus in fringes oriented to 45, 90 and 135 degrees was displayed, employing for this purpose the forced choice method between two images, one with a spatial frequency of specific contrast and the other blank, while the aberration correction device introduced different values of pure spherical aberration in the form of Zernike polynomial number 12. Specifically, values of +0.2, 0, and −0.2 micrometers for this particular polynomial were programmed. The mask of system output pupil 48 ensured that the effective size of the pupils through which the subject carried out the test was 4.5 mm. The subject had previously adjusted the distance between lenses 35, 36, which conform to the Thorner optometer, until finding his best subjective focus. The measurement of the contrast sensitivity function was carried out in a monocular manner by means of occlusion of the eye that did not intervene and also under binocular vision conditions. According to the measurements taken, a noteworthy improvement in the sensibility to contrast function was observed under binocular vision with respect to any of the monocular cases. In the case of this specific subject, the addition of 0.2 micrometers of spherical aberration produced a notable improvement in the perception of the chosen frequency. This experiment proves the viability of the invention and shows its enormous potential for carrying out numerous visual tasks in a binocular and controlled manner by means of the measurement and simultaneous manipulation of the aberrations of the two eyes.

The invention claimed is:

1. An ophthalmic instrument for measurement, control and manipulation of aberrations of eyes that enables simultaneous presentation of visual stimuli, which comprises a single retinal simultaneous illumination system, a single aberration correction device, as well as a single aberration sensor, the last two elements optically conjugated to each other by means of optical system, in that wherein said optical system acts on the light beams emerging from the eyes to prevent overlapping of said light beams on the aberration correction device and on the aberration sensor, and to make said light beams arrive separated both at the aberration correction device and the aberration sensor and wherein said optical system optically conjugates the exit pupils of the eyes on said aberration sensor and on said aberration correction device in two differentiated beams
such that the operations of measurement, control and manipulation of aberrations and presentation of stimuli are carried out in a simultaneous and binocular manner.

2. An ophthalmic instrument for measurement, control and manipulation of aberrations of eyes in accordance with claim 1, wherein the control of aberration correction device is carried out in a closed loop based on wavefront measurements obtained by sensor, which include the aberrations of the subject and those introduced by the aberration correction device.

3. An ophthalmic instrument for measurement, control and manipulation of aberrations of eyes in accordance with claim 1, wherein the control of aberration correction device is carried out in an open loop based on wavefront measurements obtained by sensor, which only include the aberrations of the subject.

4. An ophthalmic instrument for measurement, control and manipulation of aberrations of eyes in accordance with claim 1, wherein visual stimuli are projected on the retinas of the subject in a binocular manner simultaneously with the operation of measurement and manipulation of the aberrations of the eyes of the subject, and are affected by the aberrations introduced by aberration correction device.

5. An ophthalmic instrument for measurement, control and manipulation of aberrations of eyes in accordance with claim 1, wherein control and manipulation of defocus can be carried out by means of a Badal optometer.

6. An ophthalmic instrument for measurement, control and manipulation of aberrations of eyes in accordance with claim 1, wherein control and manipulation of defocus can be carried out by means of aberration corrector element.

7. An ophthalmic instrument for measurement, control and manipulation of aberrations of eyes in accordance with claim 1, wherein control and monitoring of the two pupils is conducted simultaneously by means of a single camera.

8. An ophthalmic instrument for measurement, control and manipulation of aberrations of eyes in accordance with claim 1, wherein aberration correction device is a deformable bimorph mirror.

9. An ophthalmic instrument for measurement, control and manipulation of aberrations of eyes in accordance with claim 1, wherein aberration correction device is an electrostatic deformable mirror.

10. An ophthalmic instrument for measurement, control and manipulation of aberrations of eyes, in accordance with claim 1, wherein aberration correction device is a segmented deformable mirror.

11. An ophthalmic instrument for measurement, control and manipulation of aberrations of eyes in accordance with the description of claim 1, wherein aberration correction device is a deformable mirror based on independently actuated micro-mirrors.

12. An ophthalmic instrument for measurement, control and manipulation of aberrations of eyes in accordance with claim 1, wherein aberration correction device is a liquid crystal phase modulator.

13. An ophthalmic instrument for measurement, control and manipulation of aberrations of eyes in accordance with claim 1, wherein aberration correction device is a ferroelectric liquid crystal phase modulator.

14. An ophthalmic instrument for measurement, control and manipulation of aberrations of eyes in accordance with the description of claim 1, wherein aberration correction device is a liquid crystal phase modulator on silicon.

15. An ophthalmic instrument for measurement, control and manipulation of aberrations of eyes in accordance with claim 1, wherein wavefront sensor is a Hartmann Shack sensor type.

16. An ophthalmic instrument for measurement, control and manipulation of aberrations of eyes in accordance with the description of claim 1, wherein sensor is a pyramid type wavefront sensor.

17. An ophthalmic instrument for measurement, control and manipulation of aberrations of eyes in accordance with the description of claim 1, wherein sensor is a wavefront system of the type based on wavefront curvature measurement.

18. An ophthalmic instrument for measurement, control and manipulation of aberrations of eyes in accordance with claim 1, wherein sensor is of the type that employs interferometry.

19. An ophthalmic instrument for measurement, control and manipulation of aberrations of eyes in accordance with claim 1, wherein sensor is of the type that employs double-passed retinal images.

20. An ophthalmic instrument for measurement, control and manipulation of aberrations of eyes in accordance with claim 1, wherein sensor is of the Tscherning type.

21. An ophthalmic instrument for measurement, control and manipulation of aberrations of eyes in accordance with claim 1, wherein sensor is of the crossed cylinder type.

22. An ophthalmic instrument for measurement, control and manipulation of aberrations of eyes in accordance with claim 1, wherein light source is a laser source that emits in the visible portion of the spectrum.

23. An ophthalmic instrument for measurement, control and manipulation of aberrations of eyes in accordance with claim 1, wherein light source is a laser source that emits in the infrared portion of the spectrum outside of the visible range.

24. An ophthalmic instrument for measurement, control and manipulation of aberrations of eyes in accordance with claim 1, wherein light source is a thermal source emitting in the visible spectrum.

25. An ophthalmic instrument for measurement, control and manipulation of aberrations of eyes in accordance with claim 1, wherein light source is a thermal source that emits in the infrared portion of the spectrum outside the visible range.

26. An ophthalmic instrument for measurement, control and manipulation of aberrations of eyes in accordance with claim 1, wherein control of the trajectory of the two light beams from eyes is carried out by means of reflections in mirrored prism and two independent mirrors whose position and relative angles can be manipulated.

27. An ophthalmic instrument for measurement, control and manipulation of aberrations of eyes in accordance with claim 1, wherein control of the trajectory of the two light beams from eyes is carried out by means of prisms whose position and relative angles can be manipulated.

28. An ophthalmic instrument for measurement, control and manipulation of aberrations of eyes in accordance with claim 1, wherein control of the trajectory of the two light beams from eyes is carried out by means of prisms and mirrors whose position and relative angles can be manipulated.

29. A method of measurement, control, and manipulation of aberrations of eyes which employs the ophthalmic instrument in accordance with claim 1.

* * * * *